United States Patent [19]

Palermo et al.

[11] Patent Number: 5,133,364
[45] Date of Patent: Jul. 28, 1992

[54] GUIDEWIRE EXTENSION WITH SELF-LATCHING DETACHABLE CONNECTOR

[75] Inventors: Thomas J. Palermo, Methuen, Mass.; Stephen M. Salmon, Hudson, N.H.

[73] Assignee: C. R. Bard, Inc., Murray Hill, N.J.

[21] Appl. No.: 600,243

[22] Filed: Oct. 18, 1990

Related U.S. Application Data

[63] Continuation of Ser. No. 206,008, Jun. 13, 1988, abandoned.

[51] Int. Cl.⁵ ............................................. A61B 5/00
[52] U.S. Cl. ................................ 128/772; 128/657; 604/164
[58] Field of Search ............................ 128/656–8, 128/772; 606/191–5; 604/164, 166, 170, 264, 280; 403/229, 276–7, 297, 359, 361, 372, 377, DIG. 4

[56] References Cited

U.S. PATENT DOCUMENTS

| | | |
|---|---|---|
| 642,193 | 1/1900 | Baeumle . |
| 2,105,330 | 1/1938 | Pagenkopf . |
| 2,356,835 | 8/1944 | Duckett . |
| 3,515,027 | 6/1970 | Textrom . |
| 3,517,184 | 6/1970 | Norton et al. . |
| 3,674,014 | 7/1972 | Tillander ............................ 128/657 |
| 3,888,598 | 6/1975 | Samiran et al. . |
| 4,080,706 | 3/1978 | Heilman et al. ................ 128/772 X |
| 4,183,358 | 1/1980 | Cohen ................................ 604/328 |
| 4,545,390 | 10/1985 | Leary ................................ 128/772 |
| 4,827,941 | 5/1989 | Taylor et al. .................... 128/772 X |
| 4,875,489 | 10/1989 | Messner ........................... 604/164 X |

OTHER PUBLICATIONS

Advanced Cardiovascular Systems, Inc. Brochure on DOC Guide Wire Extension dated Mar. 1988.

Primary Examiner—Ruth S. Smith
Attorney, Agent, or Firm—Wolf, Greenfield & Sacks

[57] ABSTRACT

A guidewire system for use in catheter exchanges avoids the need for a separate exchange wire by connecting an extension wire to the proximal end of the guidewire thereby increasing the effective length of the guidewire to permit a catheter exchange. The proximal end of the guidewire is attached to the distal end of the exchange wire by a disconnectable reattachable connection which avoids deformation of the connected joint.

16 Claims, 2 Drawing Sheets

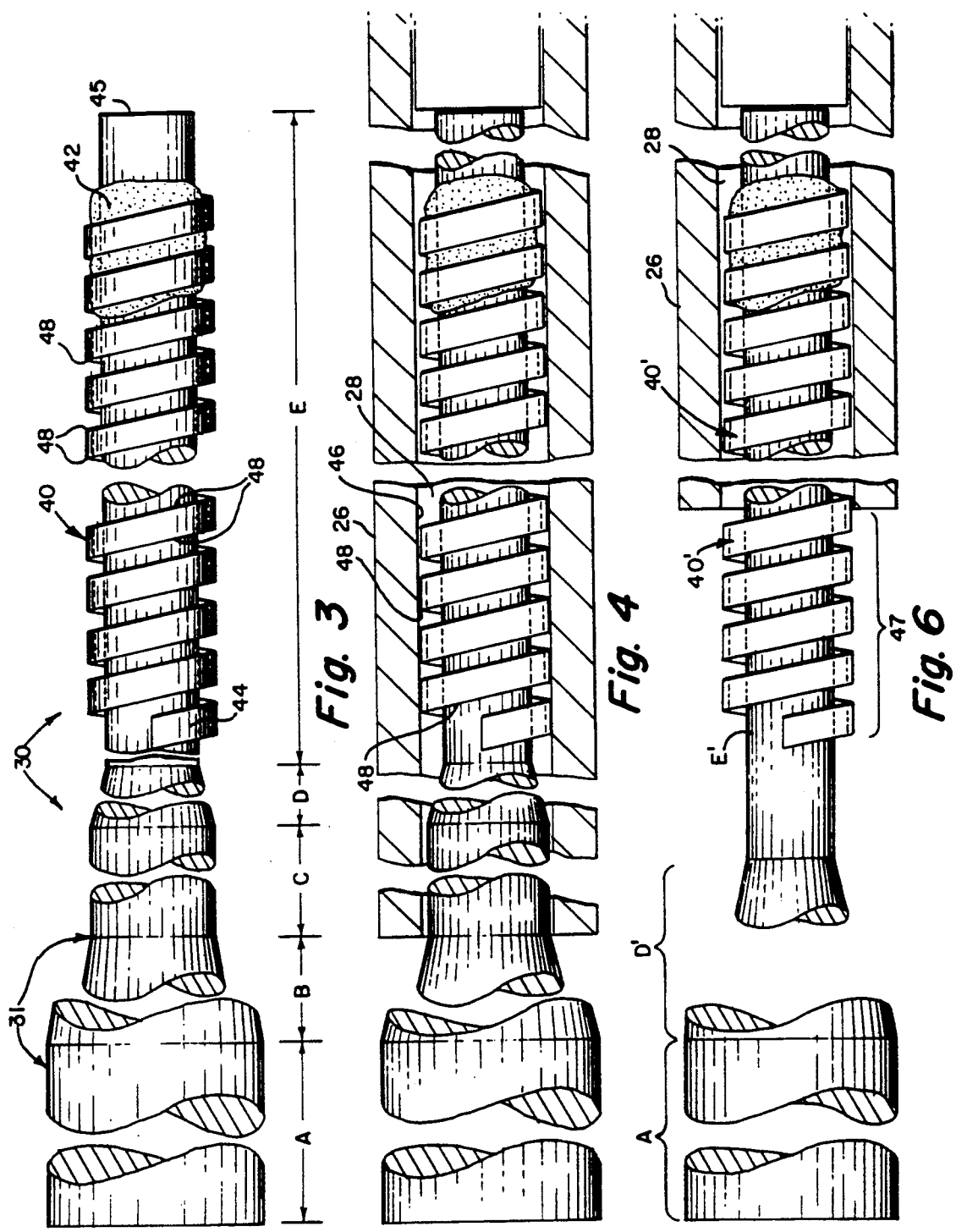

GUIDEWIRE EXTENSION WITH SELF-LATCHING DETACHABLE CONNECTOR

This application is a continuation of application Ser. No. 206,008, filed Jun. 13, 1988, now abandoned.

FIELD OF THE INVENTION

This invention relates to guidewires used in guiding of catheters and to devices and techniques for extending the effective length of the guidewires to facilitate catheter exchanges.

BACKGROUND OF THE INVENTION

In some catheterization techniques, it is desirable to use a series of catheters in order to complete effectively the procedure at hand. For example, in percutaneous transluminal coronary angioplasty procedures in which a balloon catheter is advanced into a stenosed region of the patient's coronary artery and is inflated within the stenosis to dilate the lumen of the artery, it is not uncommon for the physician to require the sequential use of several balloon dilatation catheters having balloons of progressively increasing size. Typically, such catheters are used in connection with a guidewire that extends through the catheter and serves as a guide over which the catheter may be advanced to the stenosis. When performing such a catheter exchange, it is important to do so without shifting and losing the position of the guidewire so that the guidewire may be used to guide the next catheter to the stenosis. In order to maintain guidewire position, conventional practice has been to use a relatively long exchange wire. The exchange wire, which typically is of the order of 300 cm long (as compared to a conventional guidewire length of the order of 175 cm) is first exchanged for the conventional guidewire by removing the conventional guidewire from the existing catheter and replacing it with the longer exchange wire. Then the existing catheter is withdrawn over the exchange wire, the exchange wire being sufficiently long so that it is never completely covered by the withdrawn catheter thereby enabling the exchange wire to be held in position by the physician or an assistant during the catheter withdrawal. After the initial catheter is removed, the succeeding catheter is advanced over the exchange wire which guides the second catheter to the stenosis. The exchange wire then may be removed and may be replaced with a conventional guidewire which, typically, will be more easily manipulated during the angioplasty procedure.

The foregoing procedures are time consuming and somewhat awkward. A significant advance in the technique for effecting catheter exchanges has been developed and has been in use which involves a system that enables exchange of catheters without using exchange wires. In brief, that system utilizes an extension wire that is attached to the proximal end of the guidewire already in place in the patient. That effectively extends the overall length of the guidewire to that needed for the catheter exchange. The system uses a connection in which the distal end of an extension wire is telescoped together with the proximal end of the guidewire and the junction then is crimped, thus, retaining the wires together by deforming them at their juncture. The crimp is intended to present low resistance to the catheter as it is passed over the connection. Some resistance, however, does result and it has not before been possible to completely eliminate the resistance presented by the crimp. Further inconvenience with the crimped system is that it requires the use of a separate crimping tool. When the guidewire and extension wire are detached, they cannot be reconnected or reused easily because of the deformation formed during their connection. Thus, some inconvenience is presented should it be desirable to make multiple catheter exchanges.

It is among the general objects of the invention to provide an improved connection system for a guidewire and an extension wire.

SUMMARY OF THE INVENTION

In accordance with the present invention, a connection system for a guidewire and guidewire extension utilizes a telescoping connector that is self latching, disconnectable and reconnectable without deformation of the guidewire or the extension. The connection enables the guidewire extension to be attached for a catheter exchange, then disconnected after the catheter exchange is complete to permit the guidewire and catheter to be manipulated and operated conventionally. Should another catheter exchange be required, the extension wire, which may be reused, is simply reconnected to the proximal end of the guidewire and the catheter exchange procedure may be repeated. The number of guidewire extension wire connections and disconnections are unlimited as is the number of catheter exchanges that may be performed with the system.

More particularly, the guidewire is provided with a tubular socket on the proximal end. The extension wire includes a shaft having a distal end that is dimensioned to be received in the socket. A segment of the distal end of the shaft is surrounded by a helical coil, preferably formed from rectangular cross-section wire. The coil is attached to the extension wire shaft at the distal end of the coil and is free at the proximal end of the coil to enable the coil to stretch and contract about the shaft. The distal end of the extension wire carrying the coil is easily insertable into the socket on the proximal end of the guidewire but self locks in the socket and cannot be easily withdrawn. The extension wire and guidewire may be disconnected easily, however, by twisting the guidewire extension while simultaneously withdrawing it axially from the socket. The twisting motion frees the locking engagement of the helical coil with the internal surface of the socket. In another embodiment, the extension wire also can be detached by gripping and pulling on an exposed proximal end of the helical coil.

It is among the general objects of the invention to provide an improved guidewire extension system.

A further object of the invention is to provide an improved guidewire extension system which is self-latching and does not require deformation of the joint between the guidewire and guidewire extension.

Another object of the invention is to provide a connection system for a guidewire and guidewire extension which is disconnectable and reconnectable.

Another object of the invention is to provide a guidewire and extension and connection system therefor which minimizes impedance to advancement of a catheter over the joint.

DESCRIPTION OF THE DRAWINGS

The foregoing and other objects and advantages of the invention will be appreciated more fully from the following further description thereof, with reference to the accompanying drawings wherein:

FIG. 3 is a fragmented illustration of the extension wire in accordance with the invention;

FIG. 4 is an illustration of the proximal end of the guidewire and distal end of the extension wire in a connected configuration;

FIG. 6 is a fragmented sectional illustration of the connection region of the guidewire and extension in which the helical coil has a proximal segment that protrudes outwardly of the socket to expose a proximal end of the helical coil.

DESCRIPTION OF A PREFERRED EMBODIMENT

Figure 1:
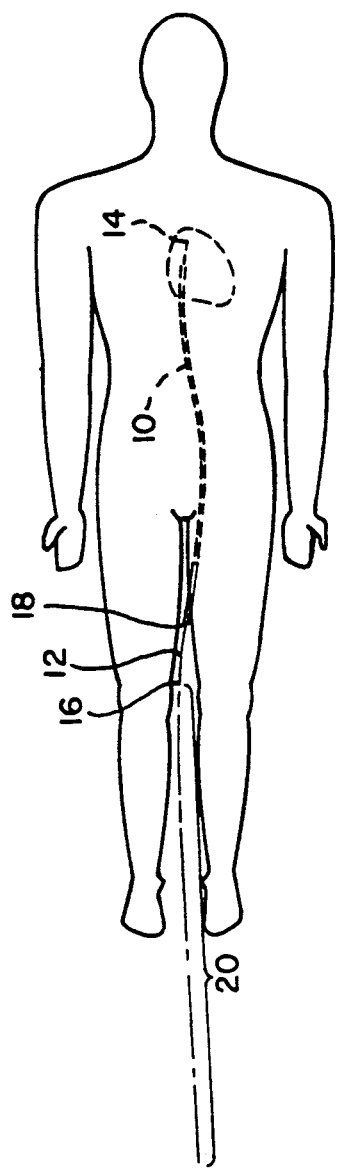
FIG. 1 is a diagrammatic illustration of a patient undergoing catheterization showing the guidewire and, in phantom, the exchange wire.

FIG. 1 illustrates in highly diagrammatic form, the catheter 10 and guidewire 12 which have been inserted into a patient's femoral artery and have been advanced through the region of the patient's heart where the desired procedure will be performed. The guidewire 12 and catheter 10 will have been inserted and placed in the artery in accordance with well known procedures. When it has been desired to perform a catheter exchange, the conventional practice has been to remove the guidewire 12 from the catheter 10 and replace it with a long exchange wire. Then the catheter 10 could be removed over the exchange wire and the next catheter could be introduced into the patient over the exchange wire. Then the exchange wire would be removed and replaced with a shorter, conventional guidewire.

In accordance with the present invention, catheters may be exchanged without requiring removal of the guidewire 12 and without requiring the involvement attendant to the use of an exchange wire. In the practice of the present invention, the guidewire 12 is connected at its proximal end to an extension wire 20 while the guidewire 12 and catheter 10 remain in the patient. The extension wire 20 is attached securely to the proximal end of the guidewire 12 and serves to extend the effective length of the guidewire 12 sufficiently to permit the catheter 10 to be withdrawn over the guidewire 12 and extension 20. Moreover, the present invention utilizes an improved connection between the guidewire and extension wire.

Figure 2:
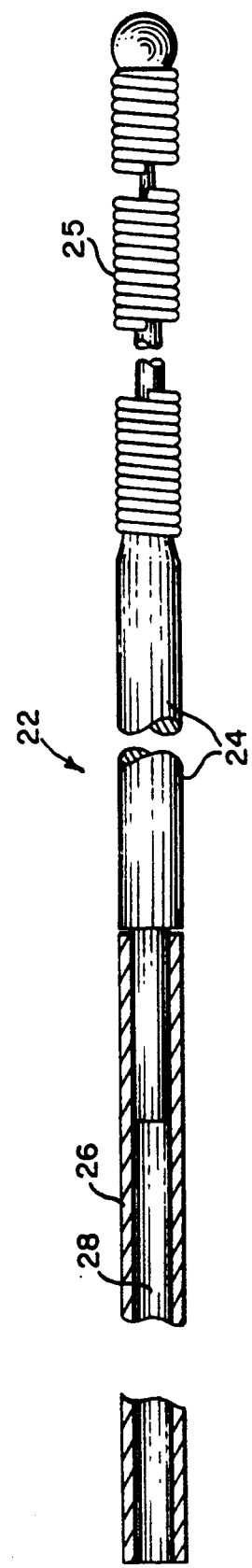
FIG. 2 is a fragmented illustration of a guidewire in accordance with the invention.

FIG. 2 shows a guidewire 22 modified in accordance with the present invention. The guidewire may be of the type illustrated in U.S. Pat. No. 4,545,390 to Leary having an elongate stainless steel shaft 24 having a proximal end (to the left in FIG. 2) and a distal end (to the right in FIG. 2) with a helical coil 25 mounted at its distal end. The guidewire, alternately, may be of a more conventional construction in which a helical coil extends substantially the full length of the guidewire. The Leary type of guidewire is disclosed by way of example. Such a guidewire may, for example, be of the order of 175 cm long and may have a shaft 24 of a diameter of 0.016". In the illustrative embodiment, the proximal end of the shaft 24 is fitted with a tubular member 26 having the same outer diameter of the shaft 24 and defining an elongate internal socket 28. The tubular member 26 may be formed from commercially available hypodermic tubing. It is believed that such tubing has a somewhat roughened internal surface which may enhance the strength of the connection. The tubular member 26 may define a socket 28 that is about 5 to 8 cm deep and 0.009" in diameter. The tubular member 26 may have a wall thickness of the order of 0.003".

FIG. 3 is a fragmented illustration of the extension wire indicated generally by the reference character 30 with the more proximal portions of the wire being axially compressed for clarity of illustration. The extension wire 30 may be considered as having a proximal end (to the left in FIG. 3) and a distal end (to the right in FIG. 3). The overall length of the extension wire 30 may be of the order of 125 cm which, when connected to a guidewire of 175 cm, results in a combined length of 300 cm which corresponds to the length of a conventional exchange wire. The extension wire 30 is formed from an elongate stainless steel shaft that may be considered as being formed of the segments A, B, C, D, and E as illustrated in FIG. 3. The proximal segment A extends over most of the length of the extension wire 30 and may be of the order of 0.016" diameter. The proximal segment A may, for example, be of the order of 117 cm long. The more distal 8 cm of the shaft, including segments B, C, D and E are of reduced diameter, generally tapering toward the distal end. Thus, the tapered segment B may be about 3 cm long and may taper down to about 0.0085" diameter. The cylindrical segment C may be about 2 cm long and about 0.0085" diameter. Cylindrical segment C merges into a distal tapered segment D that is about 1 cm long and tapers down to about 0.006" in diameter. The tapered segment D merges into distal cylindrical segment E which is 0.006" diameter and is about 2 cm long.

Mounted on the distal cylindrical segment E of the extension wire 30 is a helical coil 40 having a relaxed inner diameter slightly greater (about, 0.001" to 0.002") than the diameter of the distal segment E and a relaxed outer diameter that is equal to or just slightly greater than the inner diameter of the tubular socket 28 of the guidewire 22 to provide a light interfering fit with the socket. By way of example, the coil 40 may be approximately 1 cm long and may have an outer diameter of 0.009" and an inner diameter of 0.007". The coil 40 preferably is wound from wire that is of generally flat, rectangular cross-sectional configuration, preferably of the order of 0.001" × 0.005". It is preferred to form the coil 40 so that it is of somewhat tapering diameter, with a slightly larger diameter provided at several of the turns of the proximal end of the coil to assure a slight interference fit (of the order of 0.001" to 0.002" in diameter) between the coil and the internal surface of the socket. For example, two or three turns at the proximal end of the spring may be of slightly enlarged outer diameter, of the order of 0.010"–0.011". The coil 40 is attached at its distal end to the distal segment E as by brazing 42 to the distal segment. The proximal end 44 of the coil is free to permit the coil 40 to stretch as well as to constrict about the distal segment E. Preferably the coil 40 is of a length and is positioned so that the free proximal end 44 of the coil is not substantially more than 15 mm away from the distal tip 45 of the shaft.

The guidewire extension 30 and guidewire 22 are connected simply by inserting the distal end of the extension 30 into the tubular socket 28 at the proximal end of the guidewire 22. During such insertion, at least some of the turns of the coil 40 engage, in light interference, the internal surface 46 of the tubing 26 to cause the coil 40 to stretch longitudinally which, in turn, causes the coil 40 to constrict to a smaller diameter about the distal segment E, thereby enabling the coil 40 to be inserted into the socket 28. Once positioned in the socket, however, the coil 40 remains biased toward its expanded configuration which causes the coil 40 to bear against the internal surface 46 of the socket 28. The rectangular cross-section of the wire from which the coil 40 is formed thus defines relatively sharp, distinct edges 48 which may engage with the internal surface of the socket 28 to provide a relatively firm connection resistant to axial separation. Thus, the arrangement is self-latching and requires no other manipulation to make the connection. The guidewire and extension described herein provides a connection able to withstand more than about four pounds axial tension.

The guidewire 22 and extension 30 may be easily detached simply by applying an axial separation force while simultaneously twisting the extension 30 in a direction that will tend to constrict the spring about the distal segment of the guidewire extension. Thus, in the illustrative embodiment the extension 30 would be twisted clockwise, as seen from the left in FIG. 4, while withdrawing it axially from the socket 28. The extension 30 and guidewire 22 may be reconnected and disconnected as many times as desired, thus permitting repeated use of the extension wire. The outer diameter of the proximal segment A of the extension wire is substantially the same as the outer diameter of the guidewire 22. The connection made is smooth and continuous and does not provide any impedance to movement of the catheter over the joint.

FIG. 6 illustrates a modification that is essentially the same as the above-described embodiment except that the length and position of the helical coil 40' is such that a segment 47 at the proximal end of the coil extends proximally beyond the end of the socket 28. This arrangement provides an additional mode for detaching the guidewire and extension in which the physician may simply grip the exposed proximal segment of the coil and pull it in a proximal direction. That stretches the spring and also causes it to constrict about the distal cylindrical segment E' to a smaller outer diameter, thus disengaging from the inner surface of the socket 28 and permitting free withdrawal of the extension wire. In this configuration, the distal cylindrical segment E' on which the helical coil is mounted, is lengthened sufficiently to extend out of the proximal end of the socket 28 and also is long enough to permit the proximal segment 47 of the coil to be pulled and stretched axially in a proximal direction. In this configuration, the cylindrical segment E' may be connected by a single tapered portion D' to the proximal cylindrical segment of the shaft A, thus, omitting the intermediate step taper illustrated in FIG. 3.

Figure 5:
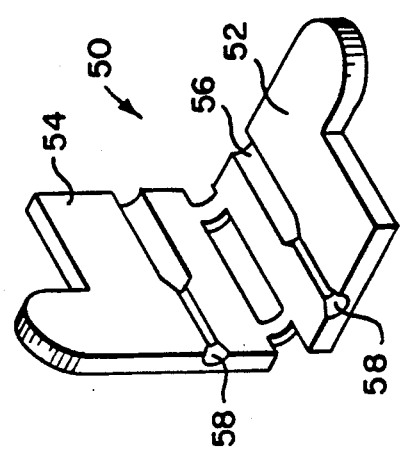
FIG. 5 is an illustration of a device to facilitate connection of the guidewire and extension wire.

It may be desirable to provide a guiding device to guide the distal end of the extension wire into the tubular socket. Such a device may be in the form of a holder 50 for the tubular member with a funnel that leads to the socket and serves to guide the distal end of the extension wire. Such a device may be made from molded plastic, for example, as illustrated in FIG. 5 which shows a pair of hinged plastic plates 52, 54 which when brought together, will define a holder groove 56 for the socket end of the guidewire and a funnel guide 58 to receive and guide the distal end of the extension wire.

From the foregoing, it will be appreciated that the invention provides an improved connection system for a guidewire and a guidewire extension that does not require the use of crimped joints or other means to deform permanently the guidewire and extension. The invention enables the extension to be connected, detached and then reconnected which permits multiple catheter exchanges should that be desired. Moreover, the joint provides a smooth uncrimped connection over which the catheters may be advanced easily and with minimal resistance.

It should be understood, however, that the foregoing description of the invention is intended merely to be illustrative thereof and that other modifications and embodiments may be apparent to those skilled in the art without departing from the spirit.

Having thus described the invention, what I desire to claim and secure by Letters Patent is:

1. A guidewire for use with a catheter and an extension for the guidewire for enabling multiple catheter exchanges comprising:

a guidewire having a proximal end and a distal end;
   an extension wire having a proximal end and a distal end;
   cooperative self-latching connector means on the proximal end of the guidewire and the distal end of the extension wire for detachably connecting the guidewire and extension wire, said connector means being so constructed and arranged as to be reconnectible after detachment, the connector means being adapted to effect a non-frictional mechanical interlock between the connectible elements thereof;
   the connector means being constructed to effect said mechanical interlock without permanent deformation of either of the proximal end of the guidewire or the distal end of the extension wire;
   the connector means being an axially telescoping construction in which the guidewire is provided with a socket at its proximal end and the extension wire has a self-latching latch member at its distal end, the self-latching latch member being received within the socket;
   the latch member comprising a helical coil having a proximal end and a distal end and being attached at its distal end to the region of the distal end of the extension wire, the proximal end of the helical coil being free to enable the helical coil to stretch axially and constrict radially about the distal end of the extension wire.

2. A guidewire and extension therefor as defined in claim 1 wherein the coil is formed from rectangular cross-section wire.

3. A guidewire and extension therefor as defined in claim 1 wherein the extension wire comprises an elongate shaft, the distal portion thereof being of reduced diameter, said helical coil being mounted on said reduced diameter distal portion.

4. A guidewire and extension therefor as defined in claim 1 wherein some of the turns of the helical coil, at the proximal end of the helical coil are of slightly larger diameter than the more distally located turns of the coil.

5. A guidewire and extension therefor as defined in claim 1 in which the diameter of the guidewire is substantially the same as the diameter of the extension, except at the distal end of the extension wire which is of reduced diameter.

6. A guidewire as defined in any one of claims 1-3 and 5 wherein the helical coil is of a length and is so mounted on the distal end of the extension wire so that when the extension wire is inserted fully into the socket of the guidewire a proximal segment of the coil will be exposed proximally of the guidewire.

7. A guidewire and extension therefor as defined in claim 6 wherein some of the turns of the helical coil that remain within the socket are of slightly larger diameter than the more distally located turns of the coil.

8. A guidewire and extension therefor as defined in claim 7 wherein the force resistant to axial separation of the guidewire and extension is substantially greater than the force for their connection.

9. A guidewire and extension therefor as defined in claim 7 wherein separation of the connected guidewire and extension requires simultaneous rotation and axial separation of the connected elements.

10. A guidewire and extension therefor as defined in claim 6 wherein the force resistant to axial separation of the guidewire and extension is substantially greater than the force for their connection.

11. A guidewire and extension therefor as defined in claim 6 wherein separation of the connected guidewire and extension requires simultaneous rotation and axial separation of the connected elements.

12. A guidewire and extension therefor as defined in any one of claims 1-5 wherein separation of the connected guidewire and extension requires simultaneous rotation and axial separation of the connected elements.

13. A guidewire and extension therefor as defined in any one of claims 1-5 wherein the force resistant to axial separation of the guidewire and extension is substantially greater than the force for their connection; and wherein separation of the connected guidewire and extension requires simultaneous rotation and axial separation of the connected elements.

14. A guidewire for use with a catheter and an extension for the guidewire for enabling multiple catheter exchanges comprising:

a guidewire having a proximal end and a distal end
an extension wire having a proximal end and a distal end;
cooperative self-latching connector elements on the proximal end of the guidewire and the distal end of the extension wire for detachably connecting the guidewire and extension wire, said connector elements being so constructed and arranged as to be reconnectible after detachment, the connector elements being adapted to effect a non-frictional mechanical interlock between the connectible elements thereof;
wherein the separation of the connected guidewire and extension requires simultaneous rotation and axial separation of the connected elements.

15. A guidewire and extension therefor as defined in claim 14 wherein the connector elements further comprise an axially telescoping construction.

16. A guidewire and extension therefor as defined in claim 15 wherein the guidewire is provided with a socket at its proximal end and the extension wire has a self-latching latch member at its distal end, the self-latching latch member being received within the socket.

* * * * *